United States Patent [19]

Del Nido et al.

[11] Patent Number: 5,407,793

[45] Date of Patent: Apr. 18, 1995

[54] AN AQUEOUS HEART PRESERVATION AND CARDIOPLEGIA SOLUTION

[75] Inventors: Pedro J. Del Nido; Hung Cao-Danh; K. Eric Sommers; Akihiko Ohkado, all of Pittsburgh, Pa.

[73] Assignee: University of Pittsburgh of the Commonwealth System of Higher Education, Pittsburgh, Pa.

[21] Appl. No.: 79,315

[22] Filed: Jun. 18, 1993

Related U.S. Application Data

[63] Continuation-in-part of Ser. No. 780,755, Oct. 18, 1991, abandoned.

[51] Int. Cl.$^6$ .......................... A01N 1/02; C12N 5/00; A61K 37/26; A61K 31/70; A61K 31/195
[52] U.S. Cl. .................................... 435/1; 435/240.2; 514/3; 514/23; 514/46; 514/561
[58] Field of Search .................... 435/1, 240.3, 240.31, 435/240.2; 514/3, 46, 23, 60, 561

[56] References Cited

U.S. PATENT DOCUMENTS

| | | | |
|---|---|---|---|
| 4,415,556 | 11/1983 | Bretschneider | 424/153 |
| 4,663,289 | 5/1987 | Veech | 435/240 |
| 4,798,824 | 1/1989 | Belzer et al. | 435/1 |
| 4,873,230 | 10/1989 | Belzer et al. | 514/60 |
| 4,920,044 | 4/1990 | Bretan, Jr. | 435/1 |
| 4,981,691 | 1/1991 | Osterholm et al. | 424/422 |
| 5,082,831 | 1/1992 | Leaf et al. | 514/56 |
| 5,145,771 | 9/1992 | Lemasters et al. | 435/1 |

FOREIGN PATENT DOCUMENTS

878297 11/1981 U.S.S.R.

OTHER PUBLICATIONS del Nido et al., "The Role of Cardioplegic Solution Buffering in Myocardial Protection", *The Journal of Thoracic and Cardiovascular Surgery*, vol. 89, No. 5, pp. 689–699, May (1985).

Jimenez et al., "Effects of Low Extracellular Calcium on Cytosolic Calcium and Ischemic Contracture", *Journal of Surgical Research*, vol. 49, pp. 252–255 (1990).

Qayumi et al., "Preservation Techniques for Heart Transplantation: Comparison of Hypothermic Storage and Hypothermic Perfusion", *J. Heart Lung Transplant*, Jul.–Aug. 1991, vol. 10, No. 4, pp. 518–526.

*Primary Examiner*—Douglas W. Robinson
*Assistant Examiner*—Susan M. Dadio
*Attorney, Agent, or Firm*—Arnold B. Silverman; Jolene W. Appleman

[57] ABSTRACT

A process for preserving a patient's organ for transplantation and cardioplegia during cardiac surgery is disclosed which includes harvesting the patient's organ for transplantation or arresting the heart during cardiac surgery, perfusing the organ or heart with an aqueous solution, and removing at least a substantial portion of the aqueous solution from the organ or heart to effect the removal of waste products from the organ before transplantation or restarting the heart. The aqueous solutions of these inventions promote anaerobic glycolysis, remove waste products from the organ and maintain the energy production capacity of the organ and are preferably comprised of about 50 to 150 millimoles of histidine per liter of the solution, at least one energy providing material for maintaining the energy production capacity of the organ, about 60 to 90 millimoles of $Na^+$ per liter of the solution, about 10 to 25 millimoles of $K^+$ per liter of the solution, and about 3 to 8 millimoles of adenosine per liter of the solution for the transplantation solution and 0.001 to 1 millimoles of adenosine per liter of the solution for cardioplegia. Sodium entry into and depolarization of the cells is resisted by the extracellular to intracellular sodium gradient and use of adenosine. The aqueous solutions of this invention have a pH of about 6.8 to 8.0 where intracellular pH is maintained by the buffering action of the histidine and the solution is preferably used at moderate hypothermia for up to 24 hours.

20 Claims, 4 Drawing Sheets

AN AQUEOUS HEART PRESERVATION AND CARDIOPLEGIA SOLUTION

CROSS REFERENCE TO RELATED APPLICATION

This application is a continuation-in-part of Ser. No. 07/780,755, filed Oct. 18, 1991, now abandoned, for "Process For Preserving An Organ And Organ Preservation Solution".

BACKGROUND OF THE INVENTION

1. Field of the Invention

This invention relates to a process for preserving a patient's organ for transplantation which includes perfusing the organ with an aqueous solution that promotes anaerobic glycolysis by providing a high energy substrate, removes waste products from the organ by buffering, and maintains the energy production capacity of the organ.

This invention also relates to a process during cardioplegia in cardiac surgery which includes perfusing the heart with an aqueous solution that arrests the heart, promotes anaerobic glycolysis by providing a high energy substrate, removes waste products from the heart by buffering and maintains the energy production capacity of the heart until the heart is restarted by reestablishing the blood flow.

2. Background Information and Description of the Prior Art

It is well known by those skilled in the art to employ during transplantation of an organ and cardioplegia during cardiac surgery a solution that will preserve the organ during the complete interruption of its blood and oxygen supply. Generally, these solutions rely on substantially arresting the organ's metabolism with the use of chemicals and by employing temperatures of 4° Centigrade and lower. This substantial slowing of the metabolism of the organ permits the energy stores in the organ at the time of harvesting to be consumed at a slower rate. Accordingly, the preservation time of these solutions is limited by the available energy stores present at the time of harvesting and the rate of their consumption. Organ preservation such as for example, preservation of the heart, is limited by the fact that currently available solutions are able only to safely preserve organs for very limited periods of time. For the heart, this time is generally less than six hours. This relatively short period of time severely limits the distance that these organs may be transported and imposes great demands upon the surgeon to complete the complex and delicate transplant surgery in an expeditious manner. Another disadvantage of these solutions is that they do not preserve the organ by promoting anaerobic glycolysis. For example, it is well known by those skilled in the art that prolonged myocardial preservation is limited by the heart's inability to maintain high energy stores and low intracellular calcium levels during ischemia. Anaerobic glycolysis, which is the only potential source of adenosine 5'-triphosphate (ATP) during ischemia, is inhibited by the accumulation of lactate and $H^+$ in the myocytes. These waste products inhibit energy production by the organ while the organ is outside of the patient's body. As a result, ATP production during ischemia is inhibited. It is known by those skilled in the art that low ATP levels are associated with detrimental morphologic changes in the heart.

U.S. Pat. No. 4,415,556 discloses a protective solution for preventing ischemia damage to organs during transplantations. It discloses a solution that includes alpha-ketoglutarate to improve aerobic metabolism during perfusion. This patent states that alpha-ketoglutarate is able to lengthen the ischemia tolerance times. It discloses, however, that the ischemia tolerance time associated with the protective solution decreases as temperature rises from 5° Centigrade to 35° Centigrade.

U.S. Pat. No. 4,663,289 discloses a process and a solution for preservation of cells in a cell culture. It discloses an ionic balanced solution that normalizes the redox state of the cell wherein the solution contains a normal Na:Cl ratio. This patent includes L-histidine $HCl.H_2O$ as a nutrient additive to the balanced salt mixture. The solution promotes aerobic metabolism by providing substrates for the mitochondria.

U.S. Pat. No. 4,920,044 discloses a hyperosmotic intracellular flush and storage solution for preserving an organ for transplantation. It states that the intracellular flush solution minimizes adenine nucleotide catabolism and post-preservation renal reperfusion injury. It also states that the intracellular flush solution comprises $KH_2PO_4$, $K_2HPO_4$, KCl, $NaHCO_3$, $KHCO_3$, mannitol, $MgSO_4$, $MgCl_2$, adenosine, allopurinol and verapamil. This patent utilizes the intracellular electrolyte flushing solution in combination with cold storage techniques for extending organ preservation.

U.S. Pat. No. 4,981,691 discloses an oxygenatable fluorocarbon nutrient cerebrospinal fluid containing electrolytes, lecithin, and amino acids. It states that the fluid may be employed for treating hypoxic-ischemic central nervous system tissue.

An article entitled "Effects of Low Extracellular Calcium on Cytosolic Calcium and Ischemic Contracture," *Journal of Surgical Research*, Vol. 49, pp. 252–255 (1990), and co-authored by E. Jimenez, M.D., et at., states that use of a low calcium cardiac arresting solution prior to ischemia improves the tolerance to ischemia.

del Nido, P., et at., "The Role of Cardioplegic Solution Buffering in Myocardial Protection", *The Journal of Thoracic and Cardiovascular Surgery*, Vol. 89, No. 5, pp. 689–699 (1985), discloses that histidine improves post-ischemic recovery of cardiac function and that zero calcium concentration in combination with a low potassium concentration is important for organ preservation.

Transplantation Art SU 878-297 teaches a heart perfusion aqueous solution which contains water, lidocaine, glucose, mannitol and phosphate.

Qayumi et al., "Preservation Techniques for Heart Transplantation: Comparison of Hypothermic Storage and Hypothermic Perfusion," *Journal of Heart-Lung Transplant*, Vol. 10, No. 4., pp. 518–526 (1991), discloses a heart perfusion solution which comprises mannitol, glucose, insulin and sodium.

In spite of the prior art disclosures, there remains a very real and substantial need for a process and aqueous solution for organ preservation and cardioplegia that promotes anaerobic glycolysis by providing a high energy substrate, removes waste products from the organ by buffering and maintains the energy production capacity of the organ.

SUMMARY OF THE INVENTION

The present invention has met the hereinbefore described needs. The present invention provides both a process and solution for cardioplegia during cardiac surgery and a process and solution for preserving a patient's heart for transplantation. These processes include arresting the patient's heart or harvesting the patient's organ, perfusing the heart or organ with the aqueous solution of this invention, and removing at least a substantial portion of the solution from the heart or organ to effect the removal of waste products from the heart or organ.

The aqueous solution of this invention comprises about 50 to 150 millimoles of histidine per liter of solution, at least one energy-providing material for maintaining the energy production capacity of the organ, about 20 to 120 millimoles of $Na^+$ per liter of said solution (preferably 60 to 90 millimoles of $Na^+$), about 5 to 30 millimoles of $K^+$ per liter of said solution (preferably 10 to 25 millimoles of $K^+$).

The aqueous solution of this invention further comprises about 4 to 16 millimoles of $Mg^{+2}$ per liter of said solution (preferably 4 to 8 millimoles), about 0.05 to 1.0 millimoles of $Ca^{+2}$ per liter of the solution (preferably 0.05 to 0.4 millimoles), about 1 to 40 units of regular insulin per liter of solution (preferably 1 to 20 units), about 1.0 to 5.0 millimoles of $PO_4^{-3}$ per liter of solution (preferably 1.25 to 3.0 millimoles) and about 10 to 20 millimoles of mannitol per liter of the solution.

For the cardioplegia solution, it is preferable to have about 0.001 to 1 millimole of adenosine per liter of solution, while for the transplantation solution about 1 to 10 millimoles of adenosine per liter of solution and preferably 3 to 8 millimoles of adenosine per liter of solution. The energy providing material of these aqueous solutions contain about 5 to 20 millimoles of glucose per liter of the solution, preferably 11 to 20 millimoles, whereby anaerobic glycolysis is promoted by the use of glucose. Depolarization of the cells of the organ and sodium entry into the cells of the organ are resisted by the extracellular to intracellular sodium gradient and use of adenosine.

Further, this invention provides a process for preserving a patient's organ for transplantation and during cardioplegia including perfusing the organ with the aqueous solution of these inventions having a pH of about 6.8 to 8.0, whereby intracellular pH is maintained within these limits by the buffering action of histidine. These processes also include perfusing the organ with the aqueous solutions of these inventions having a temperature of about 5° to 35° C. Preferably, the temperature is 10°-21° C. and most preferably 13° C.

It is an object of this invention to provide a process for preserving a patient's organ for transplantation.

It is an object of the present invention to provide an aqueous solution for organ preservation that promotes anaerobic glycolysis by providing glucose.

It is a further object of this invention to provide an aqueous solution for organ preservation that removes waste products from the patient's organ by buffering action.

It is yet a further object of the present invention to provide an aqueous solution for organ preservation that maintains the energy production capacity of the organ.

It is another object of this invention to provide a process for maintaining patient's heart during cardioplegia associated with cardiac surgery.

It is an object of the present invention to provide an aqueous solution for use during cardioplegia that promotes anaerobic glycolysis by providing glucose.

It is a further object of this invention to provide an aqueous solution for use during cardioplegia that removes waste products from the patient's heart by buffering.

It is a further object of this invention to provide an aqueous solution for use during cardioplegia that maintains the energy production capacity of the heart.

These and other objects of the invention will be more fully understood from the following description of the invention and the claims appended hereto.

DESCRIPTION OF THE PREFERRED EMBODIMENTS

Figure 1:
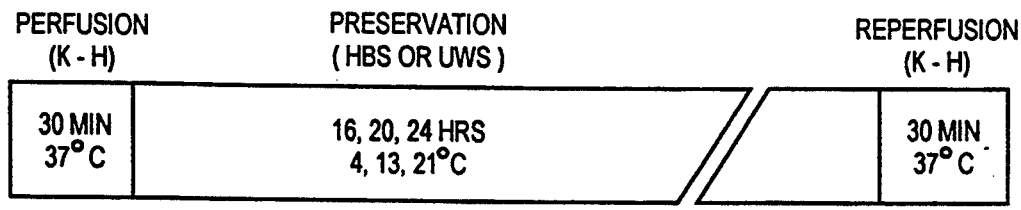
FIG. 1 illustrates schematically a flow diagram of an embodiment of the invention.

As used herein, the term "patient" includes members of the animal kingdom including but not limited to human beings.

As employed herein, "organ" includes, but is not limited to, the heart, lungs, liver, pancreas and the kidneys.

As used herein, the expression "histidine" includes histidine and the various salts of histidine including, but not limited to, histidine HCl and Na histidine.

As used herein, "sterile water" includes, but is not limited to, (a) sterile water for injection, USP, (b) sterile distilled deionized water, and (c) sterile water for irrigation.

As employed herein, "regular insulin" includes human insulin (regular) including, but not limited to, semisynthetic human insulin (regular) and recombinant DNA origin human insulin (regular).

As used herein, "cardioplegia" includes, but is not limited to, paralysis of the heart.

As used herein, "moderate hypothermia" is about 10°-21° C.

A process of one practice of this invention for preserving a patient's organ for transplantation includes harvesting the patient's organ, perfusing the organ with the aqueous solution of this invention, and removing at least a substantial portion of the aqueous solution from the organ to effect the removal of waste products from the organ. More specifically, the aqueous solution for organ preservation of this invention promotes anaerobic glycolysis, removes waste products from the organ and maintains the energy production capacity of the organ. The aqueous solution of this invention comprises (a) about 50 to 150 millimoles of histidine per liter of the solution, (b) at least one energy-providing material for maintaining the energy production capacity of the organ, (c) about 20 to 120 millimoles of $Na^+$ per liter of said solution, (d) about 5 to 30 millimoles of $K^+$ per liter of said solution, (e) about 4 to 16 millimoles of $Mg^{+2}$ per liter of said solution, (f) about 0.05 to 1.0 millimoles of $Ca^{+2}$ per liter of the solution, (g) about 1 to 40 units of regular insulin per liter of the solution and (h) about 1 to 10 millimoles of adenosine per liter of the solution. The aqueous solution of this invention preferably includes (a) about 50 to 150 millimoles of histidine per liter of solution, (b) at least one energy providing material for maintaining the energy production capacity of the organ, (c) about 60 to 90 millimoles of $Na^+$ per liter of the solution, (d) about 10 to 25 millimoles of $K^+$ per liter of the solution, (e) about 4 to 8 millimoles of $Mg^{+2}$ per liter of the solution, (f) about 0.05 to 0.4 millimoles of $Ca^{+2}$ per liter of the solution, (g) about 1 to 20 units of regular insulin per liter of the solution, and (h) about 3 to 8 millimole of adenosine per liter of the solution.

Another practice of this invention provides a process for preserving a patient's organ for transplantation including harvesting the patient's organ, perfusing the organ with the aqueous solution of this invention, removing at least a substantial portion of the aqueous solution from the organ to effect the removal of waste products from the organ, and including perfusing the organ with the aqueous solution having a pH of about 6.8 to 8.0 whereby the intracellular pH is maintained within this range by the buffering action of histidine.

It will be appreciated by those skilled in the art that the energy providing material includes monosaccharides having about six carbon atoms. The monosaccharides include such as, for example, aldoses and ketoses having about six carbon atoms.

In a preferred practice of this invention, the process for preserving a patient's organ for transplantation also includes employing about 5 to 20 millimoles of glucose, preferably 11 to 20 millimoles of glucose, per liter of this aqueous solution as the energy providing material. In a less preferred embodiment, the process of preserving a patient's organ for transplantation of this invention also includes employing 5 to 20 millimoles of fructose, per liter of this aqueous solution as the energy providing material.

Another practice of this invention provides a process for preserving a patient's organ for transplantation including perfusing the organ with the aqueous solution of this invention having a temperature of about 5° to 35° Centigrade. More preferably, this process includes perfusing the organ with the aqueous solution having a temperature of about 10° to 21° Centigrade and most preferably at 13° Centigrade. It will generally be understood by those persons skilled in the art that the process for preserving a patient's organ for transplantation of this invention includes perfusing the organ with the aqueous solution at moderate hypothermia. The process of this invention includes perfusing the organ with a volume of about 2 to 5 milliliters (ml) of the solution per gram of organ tissue perfused.

Another practice of this invention provides a process for preserving a patient's organ for transplantation which includes perfusing the organ with the aqueous solution of this invention about once each hour. The process of this invention may include perfusing the organ with the aqueous solution of this invention on an hourly cycle for at least about 24 cycles at moderate hypothermia.

Another practice of this invention includes the process for preserving a patient's organ for transplantation including perfusing the organ only one time with the aqueous solution of this invention.

It will be appreciated by those skilled in the art that the process for preserving a patient's organ for transplantation includes effecting perfusion by injecting the aqueous solution of this invention into at least one artery of the organ. The process of this invention includes effecting at least a substantial removal of the aqueous solution by gravitational flow.

Another practice of this invention includes perfusing the organ with the aqueous solution of this invention which also includes about 1 to 5 millimoles of $PO_4^{-3}$ (preferably 1.25 to 3.0 millimoles of $PO_4^{-3}$) per liter of the solution, and about 10 to 20 millimoles of mannitol per liter of the solution.

In yet another practice of this invention, the process includes perfusing the organ with the aqueous solution of this invention which also includes about 100 milligrams of lidocaine per liter of the solution.

It will generally be understood by those persons skilled in the art that the process of this invention includes surgically implanting the perfused organ into the body of the patient or the body of another patient.

The process for preserving a patient's organ for transplantation of this invention includes sterile water as the aqueous component of the solution. Also, the process of this invention preferably also includes perfusing the organ with the aqueous solution of this invention further comprising at least one member selected from the group consisting of (a) an antiseptic, such as for example trimethoprim, sulfamethoxazole, and trimethoprim-sulfamethoxazole and (b) an antibiotic, such as for example, a cephalosporin, and an aminoglycoside.

The process of this invention for maintaining a patient's heart during cardioplegia of cardiac surgery includes arresting the patient's heart by perfusing the heart with the aqueous solution of this invention, and removing at least a substantial portion of the aqueous solution from the heart to effect the removal of waste products from the heart. More specifically, the aqueous solution for cardioplegia of this invention promotes anaerobic glycolysis, removes waste products from the heart and maintains the energy production capacity of the heart. The aqueous solution of this invention comprises (a) about 50 to 150 millimoles of histidine per liter of the solution, (b) at least one energy-providing material for maintaining the energy production capacity of the heart, (c) about 20 to 120 millimoles of $Na^+$ per liter of said solution, (d) about 5 to 30 millimoles of $K^+$ per liter of said solution, (e) about 4 to 16 milligrams of $Mg^{+2}$ per liter of said solution, (f) about 0.05 to 1.0 millimoles of $Ca^{+2}$ per liter of the solution, (g) about 1 to 40 units of regular insulin per liter of the solution and (h) about 0.001 to 1 millimoles of adenosine per liter of the solution. The aqueous solution of this invention preferably includes (a) about 50 to 150 millimoles of histidine per liter of solution, (b) at least one energy providing material for maintaining the energy production capacity of the heart, (c) about 60 to 90 millimoles of $Na^+$ per liter of the solution, (d) about 10 to 25 millimoles of $K^+$ per liter of the solution, (e) about 4 to 8 millimoles of $Mg^{+2}$ per liter of the solution, (f) about 0.05 to 0.4 millimoles of $Ca^{+2}$ per liter of the solution, (g) about 1 to 20 units of regular insulin per liter of the solution, and (h) about 0.001 to 1 millimole of adenosine per liter of the solution.

Another practice of this invention provides a process for cardioplegia during cardiac surgery including arresting a patient's heart by perfusing the heart with the aqueous solution of this invention, removing at least a substantial portion of the aqueous solution from the heart to effect the removal of waste products from the heart and including perfusing the heart with the aqueous solution having a pH of about 6.8 to 8.0 whereby intracellular pH is maintained within the range by the buffering action of histidine.

In a preferred practice of this invention, the process for preserving a patient's heart during cardioplegia includes employing about 5 to 20 millimoles of glucose per liter, preferably 11 to 20 millimoles of glucose per liter, of this aqueous solution as the energy providing material. In a less preferred embodiment, the process of preserving a patient's heart during cardioplegia also includes employing 5 to 20 millimoles of fructose per liter of solution as the energy providing material.

Another practice of this invention provides a process for preserving a patient's heart during cardioplegia including perfusing the heart with the aqueous solution having a temperature of about 5° to 35° C., preferably about 10° to 21° Centigrade and most preferably at 13° Centigrade. It will be generally understood by those skilled in the art that the process for preserving a patient's heart for cardioplegia of this invention includes perfusing the heart with the aqueous solution at moderate hypothermia. The process of this invention includes perfusing the heart with a volume of about 2 to 5 milliliters of the solution per gram of heart tissue perfused. Another practice of this invention provides a process for preserving a patient's heart for cardioplegia which includes perfusing the heart with the aqueous solution of this invention about once each 20 to 40 minutes at moderate hypothermia. The process of this invention may include perfusing the heart with the aqueous solution of this invention on about 20 to 40 minute cycles for at least about 24 cycles at moderate hypothermia.

It will be appreciated by those skilled in the art that the process for preserving a patient's heart during cardioplegia includes effecting perfusion by injecting the aqueous solution of this invention into at least one artery or vein of the heart. The process of this invention includes effecting at least a substantial removal of the aqueous solution by gravitational flow.

Another practice of this invention includes perfusing the heart with the aqueous solution of this invention which also includes about 1 to 5 millimoles of $PO_4^{-3}$ (preferably 1.25 to 3 millimoles of $PO_4^{-3}$) per liter of the solution and about 10 to 20 millimoles of mannitol per liter of the solution.

In yet another practice of this invention, the process includes perfusing the heart with the aqueous solution of this invention which also includes about 100 milligrams of lidocaine per liter of the solution.

It will generally be understood by those persons skilled in the art that the process of this invention includes restarting the perfused heart by reestablishing blood flow after the cardiac surgery is complete.

The process of this invention may also include perfusing the heart with the aqueous solution of this invention further comprising at least one member selected from the group consisting of (a) an antiseptic, such as for example, trimethoprim, sulfamethoxazole, and trimethoprim-sulfamethoxazole, and (b) an antibiotic, such as for example, a cephalosporin, and an aminoglycoside.

The aqueous solution for organ preservation and cardioplegia of this invention promotes anaerobic glycolysis, removes waste products from the organ and maintains the energy production capacity of the organ. It will be appreciated, therefore, that this invention provides for a process that not only slows down the metabolic rate of the organ by maintaining intracellular homeostasis, but also promotes substrate utilization by removing waste products such as, for example, lactate and $H^+$, on a substantially continuous basis. The substantial removal of waste products involves substantially removing hydrogen ion from the cell using histidine which has the capacity to bind it and thus remove it from the cell. Because this process includes perfusing the organ with the aqueous solution of this invention at moderate hypothermia, the process is able to slow down the metabolism sufficiently but continues to maintain energy production.

In order to provide a more detailed disclosure showing the aqueous solution of this invention, examples of transplantation and cardioplegia will be provided.

Prolonged cardiac preservation during either transplantation or cardioplegia is limited by the heart's inability to maintain high energy stores and low intracellular calcium levels during ischemia. In our examples, histidine maintains intracellular pH by removing $H^+$ and lactate accruing as glucose is used as an energy substrate to make ATP or PCR. After 24 hours, the intracellular pH stays constant using histidine as a buffer to get rid of waste products. The solutions sodium and potassium concentration have to be considered together and are not similar to the traditional intracellular or extracellular concentration. The $Na^+/K^+$ concentration of the solution provides a moderately high extracellular to intracellular sodium gradient and prevents depolarization of the cells while the solution's use of adenosine prevents sodium entry into the cells. These examples also illustrate the efficiency of the highly buffered histidine and low calcium aqueous solution of this invention that is designed to promote calcium and sodium homeostasis.

EXAMPLE 1

In this example of a solution suitable for transplantation, the aqueous solution (Aq. Sol.) of this invention for the tests below has the following composition:

| | |
|---|---|
| Histidine | 100 millimoles per liter of solution |
| Glucose | 11 millimoles per liter of solution |
| $Na^+$ | 80 millimoles per liter of solution |
| $K^+$ | 22.5 millimoles per liter of solution |
| $Mg^{++}$ | 6 millimoles per liter of solution |
| $Ca^{++}$ | 0.1 millimoles per liter of solution |
| Insulin (regular) | 10 units per liter of solution |
| Adenosine | 5 millimoles per liter of solution |
| $PO_4^{-3}$ | 2.5 millimoles per liter of solution |
| Mannitol | 20 millimoles per liter of solution |
| Lidocaine | 100 milligrams per liter of solution |

Sterile Water q.s. to one liter of solution
pH of 7.8 at 21° Centigrade

EXAMPLE 2

This is an example of a solution that may be used for cardioplegia. The amount of adenosine has been adjusted for cardiac surgery.

| | |
|---|---|
| Histidine | 100 millimoles per liter of solution |
| Glucose | 11 millimoles per liter of solution |
| $Na^+$ | 80 millimoles per liter of solution |
| $K^+$ | 22.5 millimoles per liter of solution |
| $Mg^{++}$ | 6 millimoles per liter of solution |
| $Ca^{++}$ | 0.1 millimoles per liter of solution |
| Insulin (regular) | 10 units per liter of solution |
| Adenosine | 0.05 millimoles per liter of solution |
| $PO_4^{-3}$ | 2.5 millimoles per liter of solution |
| Mannitol | 20 millimoles per liter of solution |

| -continued | |
|---|---|
| Lidocaine | 100 milligrams per liter of solution |

Sterile Water q.s. to one liter of solution
pH of 7.8 at 21° Centigrade

These aqueous solutions (Aq. Sol.) were compared to an organ preservation solution of the University of Wisconsin. The University of Wisconsin states that their solution is effective for organ preservation in extended ischemia. The University of Wisconsin Solution (UWS) contained 20 millimoles of $Na^+$ per liter of solution, 140 millimoles of $K^+$ per liter of solution, 25 millimoles of $PO_4^{-3}$ per liter of solution, 5 millimoles of $Mg^{++}$ per liter of solution, 100 millimoles of lactobionate per liter of solution, 30 millimoles of raffinose per liter of solution, 5% hydroxyethyl starch (HES), and 5 millimoles of adenosine per liter of solution.

EXAMPLE 3

Hearts from New Zealand White rabbits (2 to 4 kilograms) were perfused in a Langendorff manner, well known by those skilled in the art, at 37° Centigrade with oxygenated Krebs-Henseleit buffer. After a thirty minute stabilization period, four experimental groups were created. In the first experimental group, Group I, the hearts were arrested with the aqueous preservation solution (Aq. Sol.) of this invention at 4° Centigrade. After a time period of 4 hours of ischemia, the hearts in Experimental Group I received a second infusion (20 ml) of the aqueous solution (Aq. Sol.) of this invention.

In Experimental Group II, the hearts were arrested with the aqueous solution (Aq. Sol.) of this invention at 21° Centigrade and maintained ischemic for 8 hours. The hearts in Experimental Group II received hourly infusions (20 ml) with the aqueous solution (Aq. Sol.) for each of the remaining 7 hours.

In Experimental Group III, the hearts were arrested with the University of Wisconsin solution (UWS) at 4° Centigrade and maintained ischemic for 8 hours. The hearts in Experimental Group III received a second infusion (20 ml) of the University of Wisconsin solution (UWS) after 4 hours of ischemia.

In Experimental Group IV, the hearts were arrested with the University of Wisconsin solution (UWS) at 21° Centigrade and maintained ischemic for 8 hours. The hearts in Experimental Group IV received hourly infusions (20 ml) with the University of Wisconsin solution (UWS) on an hourly basis for each of the remaining 7 hours.

Contractile function and coronary flow were measured prior to ischemia and after 30 minutes of reperfusion for each experimental group. Tissue water content was calculated for each experimental group from the wet and dry weights of the hearts after reperfusion. Pre-ischemic developed pressure was measured for each experimental group at a diastolic pressure of $8 \pm 0.5$ mmHg by an intracavitary balloon in the left ventricle. The same balloon volume was used to measure post-ischemic diastolic and developed pressure for each experimental group. For the model employed in this example, the diastolic pressure to be achieved is about 8 to 10 mmHg, the developed pressure and coronary flow to be achieved is about 100%, and the water content to be achieved is about 86%.

The results of diastolic pressure, developed pressure, coronary flow and water content are shown in Table I for each experimental group.

TABLE ONE

| Experimental Group | Temp. | Diastolic Pressure (mmHg) | Developed Pressure (%) | Coronary Flow (%) | Water Content (%) |
|---|---|---|---|---|---|
| I. Aq. Sol. (n=7) | 4° C. | 13 ± 2 | 82 ± 5 | 88 ± 4 | 90 ± 0 |
| II. Aq. Sol. (n=8) | 21° C. | 11 ± 1+ | 104 ± 3+* | 101 ± 5+* | 89 ± 1 |
| III. UWS (n=7) | 4° C. | 16 ± 1 | 82 ± 5 | 85 ± 7 | 88 ± 1 |
| IV. UWS (n=6) | 21° C. | 53 ± 6# | 0 ± 0# | 66 ± 5# | 90 ± 0 |

Values are mean ± SEM, developed pressure and coronary flow are expressed as % recovery of preischemic value
*$p<0.05$ vs. buffered solution 4° C. by ANOVA (statistical analysis of variance)
+$p<0.05$ vs. UWS solution 4° C. and 21° C. by ANOVA
$p<0.05$ vs. buffered solution 4° C. and 21° C. by ANOVA For the hearts in Experimental Group II wherein the aqueous solution (Aq. Sol.) of this invention was employed at 21° Centigrade, a complete recovery of contractile function and coronary flow (101±5%) resulted when compared to the pre-ischemic ischemic value. Also, Experimental Group II hearts had a complete recovery of developed pressure (104±3%) when compared to the pre-ischemic value. The water content of the Experimental Group II hearts showed that the Group II hearts were slightly edematous. At 4° Centigrade, the hearts of Experimental Group I that received the aqueous solution (Aq. Sol.) of this invention were able to recover developed pressure and coronary flow, but not as well as the Experimental Group II hearts that received the aqueous solution (Aq. Sol.) of this invention at 21° Centigrade. Table I shows that the University of Wisconsin Solution (UWS) was effective at only 4° Centigrade, Experimental Group III. Experimental Group II hearts that received the aqueous solution (Aq. Sol.) of the present invention at 21° Centigrade, experienced a recovery of diastolic pressure, developed pressure and coronary flow that was superior to the recovery of diastolic pressure, developed pressure and coronary flow for Experimental Group III hearts that received the University of Wisconsin Solution (UWS) at 4° Centigrade.

It will be appreciated by those skilled in the art that the highly buffered, low calcium aqueous preservation solution of this invention was effective in achieving substantially complete recovery in prolonged hypothermic ischemia. It will generally be understood by those skilled in the art that the buffering of the aqueous solution of this invention promoted anaerobic glycolysis during ischemia. The improved recovery seen at 21° Centigrade, Experimental Group II, with the aqueous solution (Aq. Sol.) of this invention is due to the fact that anaerobic glycolysis is promoted at higher temperatures. Table I shows that with the University of Wisconsin Solution (UWS), higher temperature ischemia was significantly more detrimental to Experimental Group IV.

EXAMPLE 4

Figure 2:
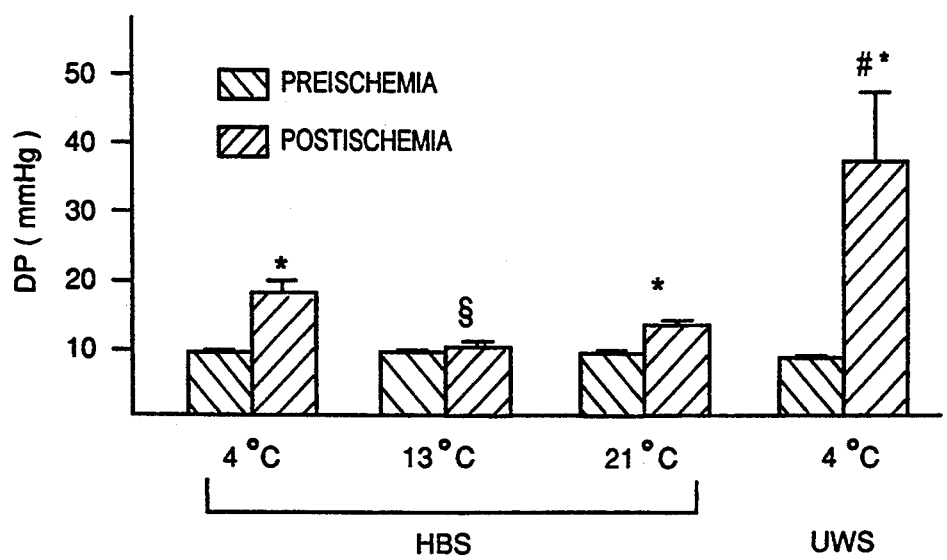
FIG. 2 is a plot showing the pre-ischemic and post-ischemic diastolic pressure of the heart.

The tests of Example 3 was rerun at 4° C., 13° C. and 21° C. using the highly buffered solution (HBS), the University of Wisconsin Solution (UWS) and the 2 to 4 kilogram New Zealand White rabbit hearts for a 16 hour preservation (ischemic) period. The 13° C. temperature tests were added to show the use of the HBS for the cardioplegia during cardiac surgery. FIG. 1 shows the schematic of the experiment. In another experiment, the White rabbit hearts were again perfused in a Langendorff manner at 37° C. with oxygenated Krebs-Henseleit buffer. The hearts were then preserved at 4° C., 13° C. and 21° C. for 16, 20, and 24 hours with the highly buffered solution (HBS). At 4° C. they were given a simple immersion in the solution while at 13° C. and 21° C., the hearts were given intermittent hourly infusion. They were then reperfused for 30 minutes at 37° C. FIG. 2 is a plot of the pre-ischemic and post-ischemic diastolic pressure of the heart after 16 hour preservation using HBS and UWS at 4° C., 13° and 21° C.; The hearts were removed and maintained at 4° C., 13° and 21° C. with hourly flushes of solution. A rise in pressure means the heart is stiffer and less supple, which is not desirable; *$p<0.05$ versus preischemic value; #$p<0.05$ versus HBS at any temperature; §$p<0.05$ versus HBS 4° and 21° C. A p value of $<0.05$ shows that there is a 95% or greater likelihood that the two values are different and, therefore, the results are different with the two solutions.

Figure 3:
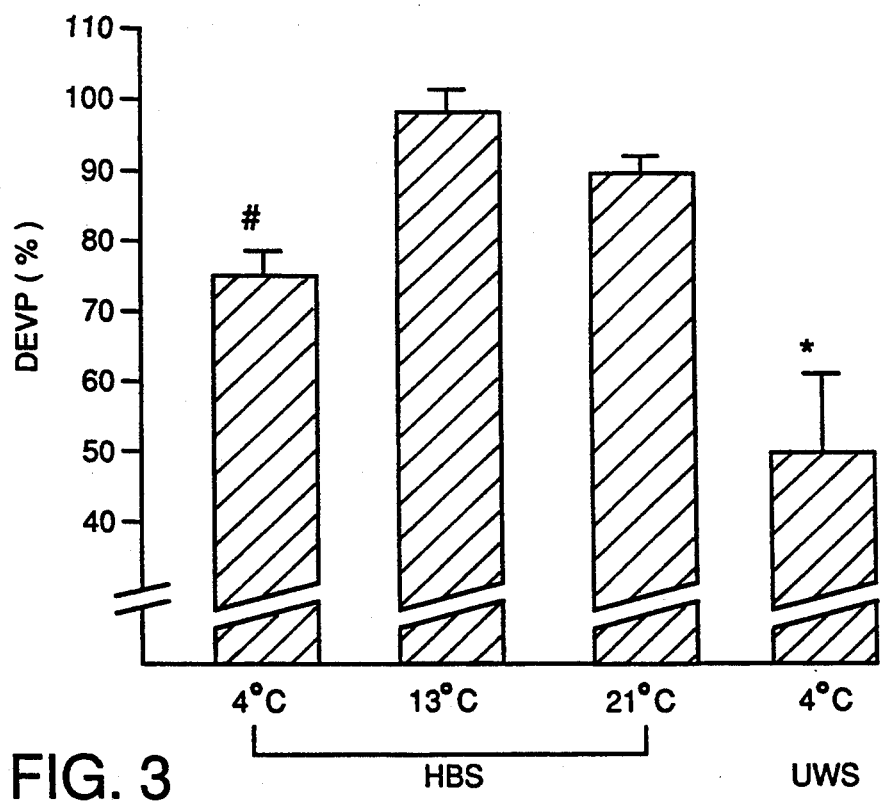
FIG. 3 is a plot showing the recovery of developed pressure of the heart.

FIG. 3 is a plot of recovery of developed pressure of the heart after a 16 hour preservation with HBS at 4° C., 13° and 21° C. and with UWS at 4° C. This measures the squeezing function of the heart and the higher the pressure the better the value. Data are expressed as mean±standard error of the mean; *$p<0.05$ versus HBS at any temperature; #$p<0.05$ versus HBS at 13° C.

Figure 4:
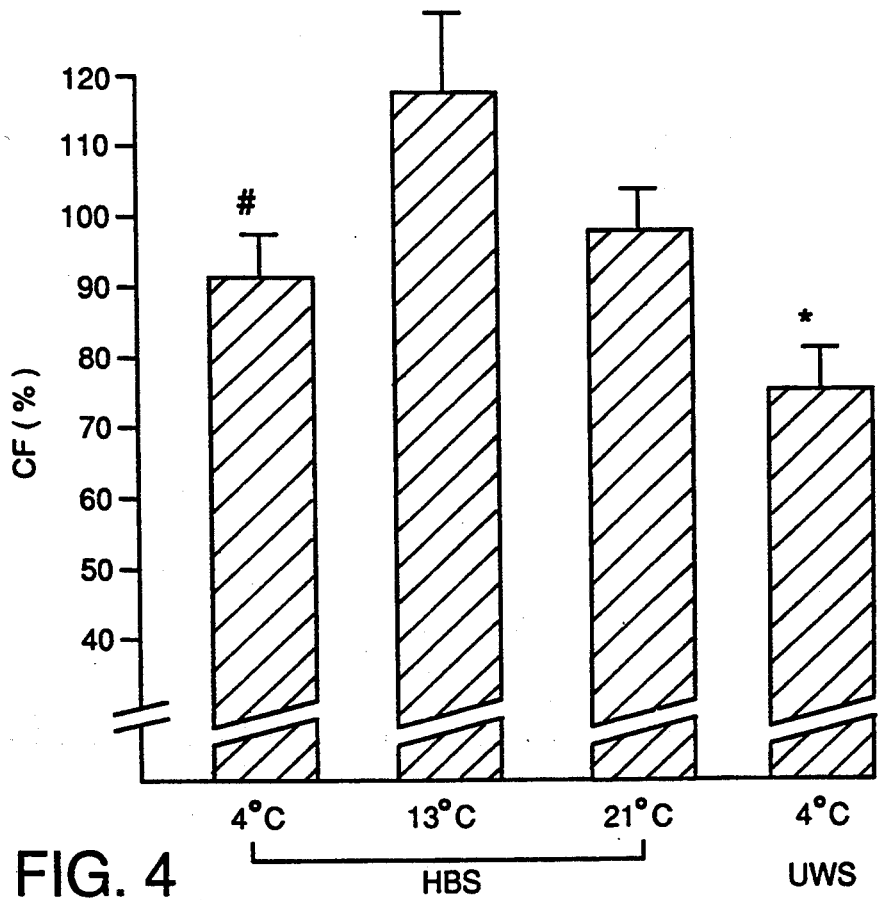
FIG. 4 is a plot showing the recovery of coronary flow of the heart.

FIG. 4 is a plot of the recovery of coronary flow of the heart after a 16 hour preservation with HBS at 4° C., 13° C. at 21° C. and with UWS at 4° C. This shows a comparison with the coronary blood flow before the heart was removed and shows the organ function. The data are expressed as mean±standard error of the mean. *$p<0.05$ versus HBS at any temperature; #$p<0.05$ versus HBS at 13° C.

Figure 5:
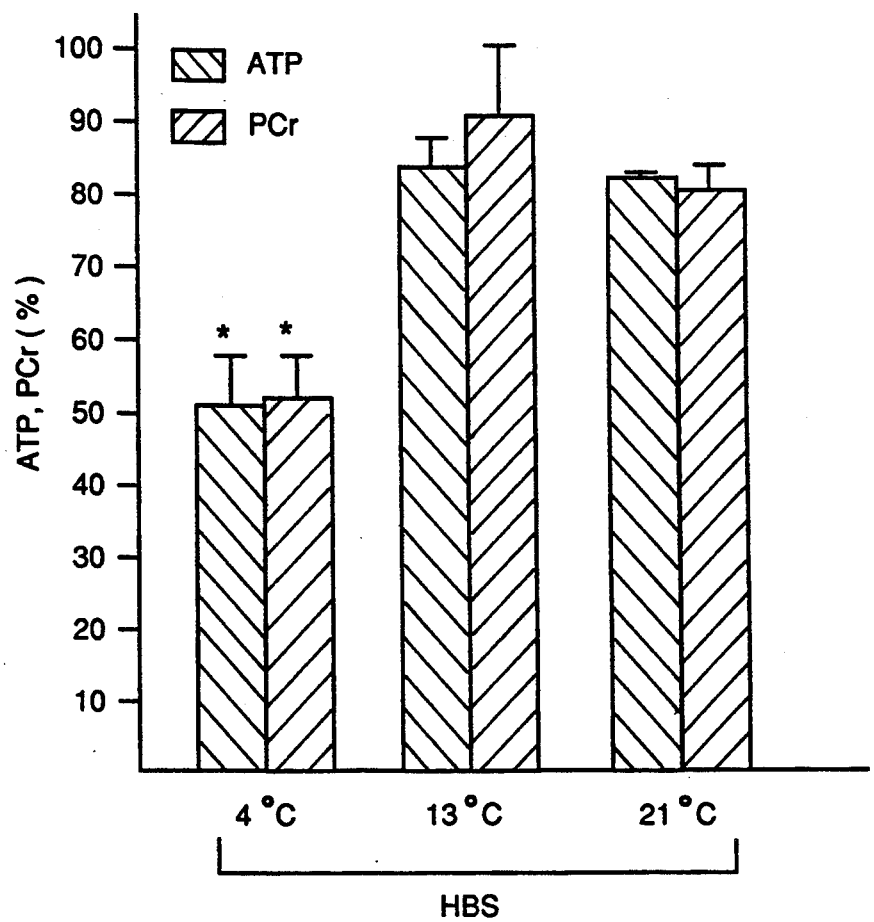
FIG. 5 is a plot showing the recovery of ATP and PCr of the heart.

FIG. 5 is a plot of the recovery of ATP and PCr of the heart after 16 hour preservation by HBS at 4° C., 13° and 21° C. This shows the amount of high energy substrate the heart can make after it is out of the body. It is measured in % of what was originally there. The data are expressed as mean±standard error of the mean. *$p<0.05$ versus 13° C. and 21° C.

Figure 6:
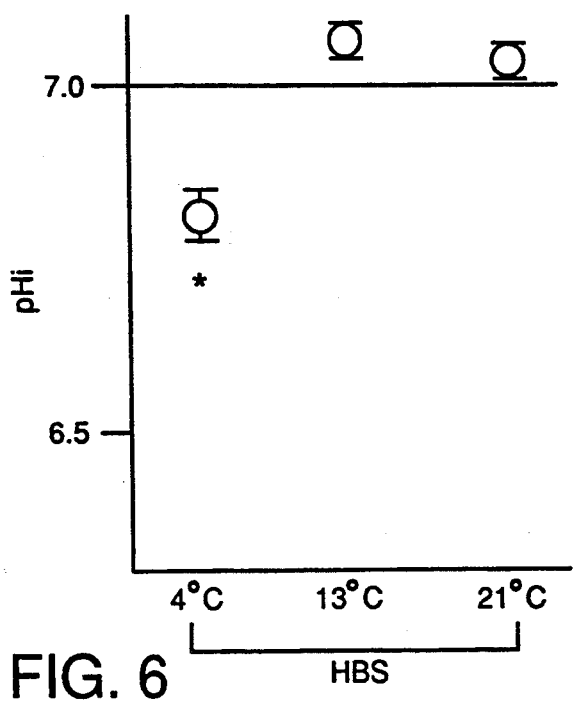
FIG. 6 is a plot showing the recovery of the intracellular pH of the perfused heart.

FIG. 6 is the recovery of the pHi (intracellular pH) after 16 hour preservation by HBS at 4° C., 13° C. and 21° C. As glucose is used the $H^+$ increases but histidine buffers it. At 13° C. after 16 hours the phi is same level as before. The data are expressed as mean±standard error of the mean. *$p<0.05$ versus 13° C. and 21° C.

TABLE II

| WATER CONTENT(%) OF THE HEART | | | |
|---|---|---|---|
| (a) 16 hour preservation | | (b) 13° C. preservation | |
| UWS 4° C. | 89.5 ± 0.4 | HBS 16 hr | 88.7 ± 0.4 |
| HBS 4° C. | 88.6 ± 0.4 | HBS 20 hr | 89.4 ± 0.5 |
| HBS 13° C. | 88.7 ± 0.4 | HBS 24 hr | 88.7 ± 0.4 |
| HBS 21° C. | 89.4 ± 0.3 | | |

(a) after 16 hour preservation.
(b) after preservation by HBS at 13° C. for 16, 20, and 24 hours. Data are expressed as mean ± standard error of the mean.

This table shows the water content of the heart following this experiment. (a) shows the water content in % after 16 hour preservation. At 4° C. there was a single cold flush and at 13° and 21° C. there were hourly flushes. (b) shows preservation by HBS at 13° C. for 16, 20, and 24 hours with hourly flushes. The data are expressed as mean±standard error of the mean.

EXAMPLE 5

Figure 7:
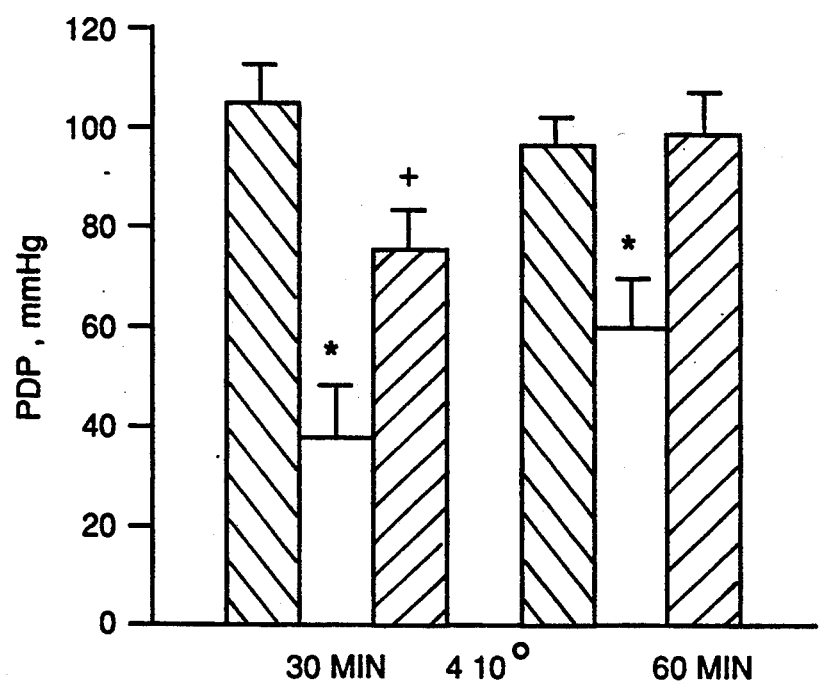
FIG. 7 is a plot showing peak developed pressure.

Another example was done using new born piglet hearts which generally prefer glucose. They were perfused using the procedure of Example 3 once at 4° C. and stored at 4° C. for 20 hours before being reperfused. FIG. 7 shows the peak developed pressure after being reperfused for 30 minutes and 60 minutes. The block column is the control, the white column UWS and the stripped column HBS.

As FIG. 7 shows, when the highly buffered solution (HBS) was given for 20 hours to arrested newborn piglet hearts, which are naturally dependent on glucose, peak developed pressure is near normal when the hearts are reperfused even under the worse conditions at 4° Centigrade. The set of tests described above and the results given in the figures show that the HBS solution is very suitable for cardioplegia during cardiac surgery.

The above experimental studies show that at moderate hypothermia (10° to 21° Centigrade) and most preferably 13° Centigrade with the HBS of the invention (Example 1), the organ can be arrested for up to 24 hours and returned to near normal usage.

This invention has solved a long standing need that has burdened the organ transplantation field and the cardiac surgery field for some time. Previously, once an organ was taken out for transplantation, it had to be transplanted within a very short time into another patient. However, with hourly flushes at moderate hypothermia (10° to 21° Centigrade), a better match for each organ can be found leaving more time to both transport and for transplantation of the organ. This also holds true for cardiac surgery where cardioplegia occurs, since the better shape the heart is in after it has been restarted, the better chance for survival of the patient. This leaves the physician with adequate time during the cardiac surgery.

It will be understood that the aqueous solutions of the present invention promotes substrate utilization for high energy phosphate production necessary for long term myocardial preservation. It will also be understood that the process for preserving a patient's organ for transplantation of the present invention includes perfusing the organ with an aqueous solution that promotes anaerobic glycolysis, removes waste products from the organ, and maintains the energy production capacity of the organ.

It will also be understood that the process for preserving a patient's heart during cardioplegia of cardiac surgery includes arresting the heart, and perfusing the heart with an aqueous solution that promotes anaerobic glycolysis, removes waste products from the heart, and maintains the energy production capacity of the heart.

Whereas particular practices of this invention have been described above for purposes of illustration, it will be evident to those persons skilled in the art that numerous variations of the details of the present invention may be made without departing from the invention as defined in the appended claims.

What is claimed is:

1. An aqueous heart preservation solution consisting essentially of:
   about 50 to 150 millimoles of histidine per liter of said solution;
   at least one energy providing material for maintaining energy production capacity of the organ;
   about 20 to 120 millimoles of Na+ per liter of said solution;
   about 5 to 30 millimoles of K+ per liter of said solution;
   about 1 to 10 millimoles of adenosine per liter of said solution;
   about 1 to 20 units of regular insulin per liter of said solution: and
   about 100 milligrams of lidocaine per liter of said solution wherein said heart preservation solution promotes anaerobic glycolysis, removes waste products from the organ by buffering, maintains the energy production capacity of the organ, and resists sodium entry into the cell during ischemia and reperfusion.

2. The aqueous solution of claim 1, wherein the amount of
   said Na+ is about 60 to 90 millimoles per liter of said solution;
   said K+ is about 10 to 25 millimoles per liter of said solution; and
   said adenosine is about 3 to 8 millimoles per liter of said solution.

3. The aqueous solution of claim 2, wherein said solution has a pH of about 6.8 to about 8.0.

4. The aqueous solution of claim 3, wherein said energy providing material comprises about 5 to 20 millimoles of glucose per liter of said solution, whereby anaerobic glycolysis is promoted by use of said glucose.

5. The aqueous solution of claim 3, wherein said energy providing material comprises about 5 to 20 millimoles of fructose per liter of said solution, whereby anaerobic glycolysis is promoted by use of said fructose.

6. The aqueous solution of claim 4, wherein said solution further includes:
   about 4 to 16 millimoles of $Mg^{+2}$ per liter of said solution;
   about 0.05 to 1.0 millimoles of $Ca^{+2}$ per liter of said solution;
   about 1.0 to 5.0 millimoles of $PO_4^{-3}$ per liter of said solution; and
   about 10 to 20 millimoles of mannitol per liter of said solution.

7. The aqueous solution of claim 6, wherein the amount of
   said $Mg^{+2}$ is about 4 to 8 millimoles per liter of said solution;
   said $Ca^{+2}$ is about 0.05 to 0.4 millimoles per liter of said solution; and
   said $PO_4^{-3}$ is about 1.25 to 3.0 millimoles per liter of said solution.

8. The aqueous solution of claim 7, wherein said aqueous solution further includes sterile water.

9. The aqueous solution of claim 8, wherein said solution further includes an antiseptic.

10. The aqueous solution of claim 8, wherein said solution further includes an antibiotic.

11. An aqueous cardioplegia solution consisting essentially of:
    about 50 to 150 millimoles of histidine per liter of said solution;
    at least one energy providing material for maintaining energy production capacity of the heart;
    about 20 to 120 millimoles of Na+ per liter of said solution;
    about 5 to 30 millimoles of K+ per liter of said solution;
    about 0.001 to 1 millimole of adenosine per liter of said solution;
    about 1 to 20 units of regular insulin per liter of said solution; and
    about 100 milligrams of lidocaine per liter of said solution wherein said aqueous solution for cardioplegia promotes anaerobic glycolysis, removes waste products from the organ by buffering, maintains the energy production capacity of the organ, and resists sodium entry into the cell during ischemia and reperfusion.

12. The aqueous solution of claim 11; wherein the amount of
    said Na+ is about 60 to 90 millimoles per liter of said solution; and
    said K+ is about 10 to 25 millimoles per liter of said solution.

13. The aqueous solution of claim 12, wherein said solution has a pH of about 6.8 to about 8.0.

14. The aqueous solution of claim 13, wherein said energy providing material comprises about 5 to 20 millimoles of glucose per liter of said solution, whereby anaerobic glycolysis is promoted by said glucose.

15. The aqueous solution of claim 13, wherein said energy providing material comprises about 5 to 20 millimoles of fructose per liter of said solution, whereby anaerobic glycolysis is promoted by said fructose.

16. The aqueous solution of claim 14, wherein said solution further includes:
    about 4 to 16 millimoles of $Mg^{+2}$ per liter of said solution;
    about 0.05 to 0.4 millimoles of $Ca^{+2}$ per liter of said solution;
    about 1.0 to 5.0 millimoles of $PO_4^{-3}$ per liter of said solution; and
    about 10 to 20 millimoles of mannitol per liter of said solution.

17. The aqueous solution of claim 16, wherein the amount of said $Mg^{+2}$ is about 4 to 8 millimoles per liter of said solution;
    said $Ca^{+2}$ is about 0.05 to 0.4 millimoles per liter of said solution; and
    said $PO_4^{-3}$ is about 1.25 to 3.0 millimoles per liter of said solution.

18. The aqueous solution of claim 16, wherein said aqueous solution further includes sterile water.

19. The aqueous solution of claim 18, wherein said solution further includes an antiseptic.

20. The aqueous solution of claim 18, wherein said solution further includes an antibiotic.

* * * * *